(12) United States Patent
Tonnessen et al.

(10) Patent No.: US 8,003,401 B2
(45) Date of Patent: *Aug. 23, 2011

(54) CARBON DIOXIDE SENSOR AND METHOD OF DETERMINING PARTIAL PRESSURE OF CARBON DIOXIDE

(75) Inventors: Tor Inge Tonnessen, Oslo (NO); Peyman Mirtaheri, Oslo (NO)

(73) Assignee: Alertis Medical AS (NO)

( * ) Notice: Subject to any disclaimer, the term of this patent is extended or adjusted under 35 U.S.C. 154(b) by 0 days.

This patent is subject to a terminal disclaimer.

(21) Appl. No.: 12/577,897

(22) Filed: Oct. 13, 2009

(65) Prior Publication Data

US 2010/0044226 A1 Feb. 25, 2010

Related U.S. Application Data

(63) Continuation of application No. 10/356,951, filed on Feb. 3, 2003, now Pat. No. 7,622,304, which is a continuation of application No. 09/743,971, filed as application No. PCT/GB99/02315 on Jul. 19, 1999, now Pat. No. 6,541,268.

(30) Foreign Application Priority Data

Jul. 17, 1998 (GB) .................................. 9815667.2

(51) Int. Cl.
*G01N 33/00* (2006.01)

(52) U.S. Cl. .................. 436/133; 422/82.01; 422/82.02; 422/82.04

(58) Field of Classification Search .................. 436/133; 422/82.01, 82.02, 82.04
See application file for complete search history.

(56) References Cited

U.S. PATENT DOCUMENTS

| | | | |
|---|---|---|---|
| 4,197,853 A | 4/1980 | Parker | |
| 4,324,256 A | 4/1982 | Vesterager | |
| 4,452,672 A | 6/1984 | Parker | |
| 5,244,561 A | 9/1993 | Calzi | |
| 5,526,809 A | 6/1996 | Fiddian-Green | |
| 6,541,268 B1 * | 4/2003 | Tonnessen et al. | 436/133 |
| 7,622,304 B2 * | 11/2009 | Tonnessen et al. | 436/133 |

FOREIGN PATENT DOCUMENTS

| | | |
|---|---|---|
| JP | 56070756 | 6/1981 |
| JP | 58058457 | 4/1983 |
| JP | 62259053 | 11/1987 |
| JP | 07231885 | 9/1995 |

* cited by examiner

*Primary Examiner* — Sam P Siefke

(74) *Attorney, Agent, or Firm* — Cantor Colburn LLP

(57) ABSTRACT

A carbon dioxide sensor and a method of detecting carbon dioxide using the sensor are provided, the sensor includes a closed chamber having as a wall portion thereof a substantially watertight, carbon dioxide-permeable membrane, two electrodes disposed in the chamber, and a film of substantially electrolyte-free liquid disposed in the chamber capable of simultaneously contacting the membrane and both of the electrodes.

6 Claims, 12 Drawing Sheets

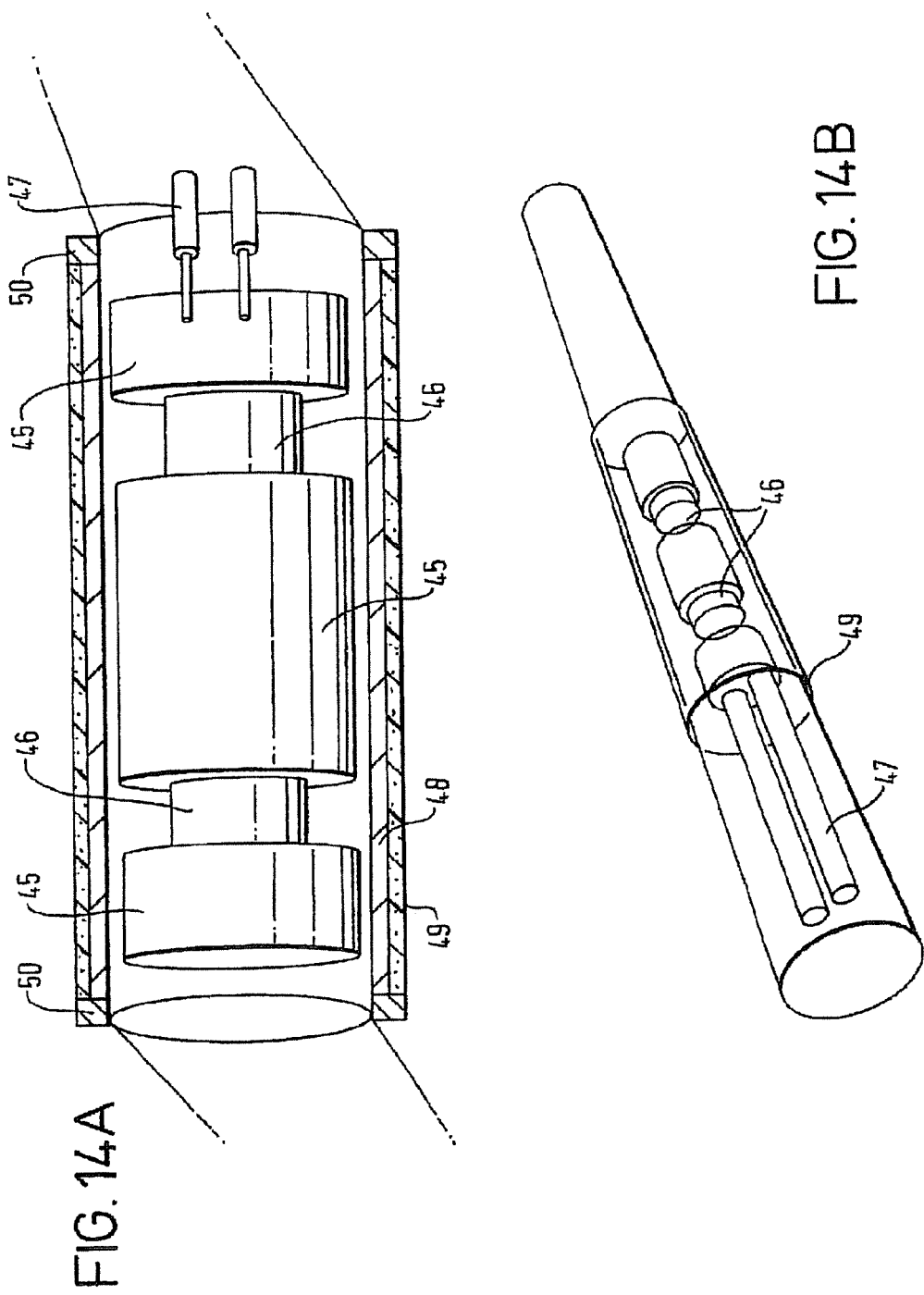

CARBON DIOXIDE SENSOR AND METHOD OF DETERMINING PARTIAL PRESSURE OF CARBON DIOXIDE

CROSS-REFERENCE TO RELATED APPLICATION

This application is a continuation of, and claims the benefit of, U.S. patent application Ser. No. 10/356,951 Ser. No. 7,622,304 filed on Feb. 3, 2003, which is itself a continuation of application Ser. No. 09/743,971 and claims benefit of, U.S. Pat. No. 6,541,268 filed on Mar. 13, 2001 and issued on Apr. 1, 2003. Both U.S. patent application Ser. No. 10/356,951 and U.S. Pat. No. 6,541,268 are herein incorporated by reference in their entirety.

FIELD OF INVENTION

The invention relates to a sensor for the partial pressure of carbon dioxide ($pCO_2$) in particular in vivo or ex vivo, e.g. in or on the surfaces of body tissues or organs, in blood or in the airflow from the lungs, and to a method of measuring $pCO_2$.

DESCRIPTION OF RELATED ART

Ischemia, localized diminution in blood flow, is the most prevalent cause of death in the western world. Thus for example myocardial infarction, cerebral infarction and other conditions characterised by hypoperfusion to one or more organs are major factors in mortality.

Reperfusion, reversal of ischemia, is frequently possible if an ischemia is detected in time. Thus early detection of ischemia followed by appropriate chemical treatment (e.g. with an agent such as streptokinase, urokinase or t-PA which serves to lyse thrombi or emboli) or surgical intervention can save the affected organ as well as the patient's life.

While the heart may be monitored continuously for ischemias using an electrocardiograph (ECG), other organs may become severely ischemic and incur irreversible damage before any symptom is detected. Indeed many organs are "silent" when it comes to ischemia. The phenomenon of silent myocardial infarction is now well recognised. Furthermore, liver and kidney may be severely ischemic without alerting symptoms before the organ damage is irreversible.

It is known that there is a distinct correlation between $pCO_2$ in or on the surface of an organ and the presence of an ischemia in that organ. During tissue metabolic acidosis, e.g. during the anaerobic metabolism that occurs in an ischemia in any organ or tissue, large quantities of carbon dioxide are formed. $CO_2$ is in practical terms freely cell-membrane permeable and since in the ischemia blood flow to transport away the $CO_2$ is absent or restricted, $CO_2$ build up in the ischemic tissue will occur and $pCO_2$ in or on the ischemic tissue will increase. Generally, in the healthy body, the maximum $pCO_2$ in blood (venous blood) is 7-10 kPa and the maximum $pCO_2$ in healthy (aerobic) tissue is some 1-6 kPa higher, although the maxima may vary from organ to organ, e.g. 8-12 kPa for kidney, 7-11 kPa for liver, 8-12 kPa for intestinal serosa, and 12-19 kPa for intestinal mucosa. Where oxygen supply falls below the critical oxygen delivery level, $pCO_2$ values measured in the tissue may rise by 3 to 10 times and the elevated $pCO_2$ levels give a clear indication of anaerobic metabolism and hence, if appropriate, of ischemia.

Sensors for $pCO_2$ are available: however these are generally bulky, often involve relatively complex glass electrodes, routinely do not give stable reproducible readings (i.e. suffer problems of drift), and are sufficiently expensive as to mandate reuse and thus the need to be repeatedly sterilized.

There is thus a need for simple, small, and preferably disposable, sensors which can be used generally to determine $pCO_2$, e.g. in order to detect ischemias.

SUMMARY OF INVENTION

We have now developed a simple sensor particularly suitable for $pCO_2$ measurement, especially as part of a technique for monitoring for ischemias.

Viewed from one aspect therefore the invention provides a carbon dioxide sensor comprising a closed chamber having as a wall portion thereof a substantially water-tight, carbon dioxide-permeable membrane and containing two electrodes, said chamber containing a film of substantially electrolyte-free liquid capable of simultaneously contacting said membrane and both of said electrodes.

By substantially electrolyte-free, it is meant that the liquid has an osmolality no greater than that at 37° C. of an aqueous 5 mM sodium chloride solution, preferably no more than that of a 500 uM sodium chloride solution, more especially no more than that of a $10^{-5}$ to $10^{-6}$ M HCl solution.

Viewed from an alternative aspect the invention provides a carbon dioxide sensor comprising a first electrode, a second electrode, a carbon dioxide permeable membrane, a liquid in electrical contact with said first and second electrodes and said membrane, means for applying an alternating electrical potential to said first and second electrodes whereby to cause an alternating current in said liquid, and means for generating a signal indicative of the conductance of said liquid, wherein said liquid is reactive with carbon dioxide to alter its conductance and wherein said electrical potential may, in an exemplary embodiment, have a frequency of 20 to 10000 Hz, preferably 100 to 4000 Hz.

Viewed from a still further aspect the invention provides, a carbon dioxide sensor comprising a first electrode, a second electrode, a carbon dioxide permeable membrane, a liquid in electrical contact with said first and second electrodes and said membrane, and wall means which together with said membrane and said electrodes define a chamber enclosing said liquid such that in the electrical path between said electrodes through said liquid the electrical resistance of said liquid at each of said electrodes is less than in a portion of said liquid in contact with said membrane. This increased electrical resistance relative to the resistance at the electrodes may be achieved by restricting the cross sectional area of the electrical path through the liquid between the electrodes at a zone in which the liquid is in contact with the membrane, e.g. by decreasing the depth of the liquid for a part of the path between the electrodes, and/or by ensuring a relatively large area of contact between each electrode and the liquid.

Preferably the liquid in contact with the electrodes is aqueous and especially preferably it is water, substantially electrolyte-free as defined above. Other solvents that react with $CO_2$ to increase or decrease their conductance, e.g. by the production or neutralization of ions, may likewise be used. In practice, however, deionized or distilled water with or without the addition of a strong acid (e.g. HCl) to a concentration of 0.1 to 100 uM, preferably 0.5 to 50 uM, more especially about 1 uM, has been found to function particularly well. The function of this small addition of acid is generally to maintain the pH of the liquid at 6 or below to avoid significant contributions to conductance by hydroxyl ions and to maintain the linearity of the measurements of $pCO_2$.

The sensors of the invention are provided with or are connectable to an electrical power source arranged to apply an alternating electrical potential across the electrodes which may, in an exemplary embodiment, have a frequency of 20 to 10000 Hz, preferably 50 to 4000 Hz, more especially 100 to 1200 Hz.

For particularly high accuracy, the potential or current across the electrodes (and hence the resistance or conductance of the liquid between the electrodes) is determined using a lock-in amplifier set to the same frequency as that of the voltage generator.

Furthermore in an exemplary embodiment of the sensor, or in a sensor-plus-detector system, a passive high pass filter may be employed (e.g. a capacitor and a resistor) to screen out current with a frequency less than 20 Hz, preferably less than 150 Hz.

The power source may be an AC power source or alternatively a DC source in conjunction with an oscillator, i.e. a combination which together constitutes an AC power source.

The power supply is preferably such that the maximum current density through the liquid at the electrodes is no more than 50 $A/m^2$, preferably no more than 30 $A/m^2$, more preferably no more than 20 $A/m^2$, in particular no more than 10 $A/m^2$, and most preferably about 1 $A/m^2$ or below. Higher current density values of 20 $A/m^2$ or greater should only be used at the higher frequencies, e.g. 1-10 kHz. The smallest maximum current density is determined by detection limits, but values down to 108 $A/m^2$ are usable. The smallest maximum current density however will generally be at least 0.1 p·$A/m^2$.

By operating at such current densities and voltage frequencies, and by appropriate construction, the sensors of the invention can, unlike the prior art devices, determine the conductance/resistance of the liquid into which the $CO_2$ migrates without any significant loss of accuracy arising as a result of the electropolarization of the electrodes.

Electropolarization effects are considerably reduced by increasing the surface area of the electrodes in contact with the liquid, e.g. by siting the electrodes in wells disposed away from the plane of the membrane or by using non planar electrode surfaces, e.g. rough or textured surfaces. In general therefore it is desirable to have as large a surface area of electrode:liquid contact as possible, as large a surface area of membrane:liquid contact as possible, and as shallow as possible a liquid depth over as much as possible of its area of contact with the membrane. In this way the response time is reduced, electropolarization is reduced, lower frequencies may be used and stray capacitance effects are considerably reduced.

The resistance of the liquid at the membrane and between the electrodes may be increased by the use of means to define liquid channels across the membrane between the electrodes, e.g. by disposing the membrane across or adjacent an insulating chamber wall portion in which such channels are formed, for example by etching. Likewise a porous spacer may be disposed between the membrane and the chamber wall to define the depth of the liquid.

Indeed, such spacers are important to use where, under the pressure conditions experienced in use, the membrane is sufficiently flexible and the liquid depth behind the membrane sufficiently small, for the measured conductance to vary with pressure. However, where a flexible non-$CO_2$ permeable membrane is used, the omission of the spacer or the use of an apertured spacer which allows the membrane to deform under pressure leads to a device in which determination of conductance may be used as a means of measuring pressure, e.g. in vivo.

Thus viewed from a further aspect the invention provides a pressure sensor comprising a first electrode, a second electrode, a flexible membrane, preferably a gas impermeable membrane, and an electrically conductive liquid in contact with said electrodes and said membrane the conductance whereof is altered by pressure induced deformation of said membrane. Such a pressure sensor may be constructed and operated along the same principles as the $pCO_2$ sensors of the invention.

The power source and the detector circuitry may, if desired, be included in the sensor of the invention. In this case, if it is desired that the sensor be wire (i.e. lead) free, it will preferably also be provided with means enabling the signal to be detected remotely, e.g. a transmitter, for example a RF transmitter. In this way the sensor may be implanted, for example in an at-risk patient.

The sensors according to the invention are readily produced having a size and configuration particularly suited to measuring $pCO_2$ (or pressure) on the surface of or in an organ, duct or tissue, e.g. brain, heart, liver, kidney, gut or muscle. This is of particular interest as it allows the functioning of the organ, duct or tissue to be monitored, e.g. during and after transplant, in intensive care, following injury, etc. and so allows early detection of ischemias.

Viewed from another aspect the invention provides a method of determining $pCO_2$, e.g. to detect or monitor ischemias, in a human or vascularized non-human animal body (e.g. a mammal, bird or reptile), said method comprising determining a partial pressure of carbon dioxide at a site in said body using a sensor according to the invention, whereby to detect ischemias in said body. The partial pressure determined according to the method of the invention may be a quantified value or it may simply be an indication that $pCC_2$ is above or below one or more threshold values indicative of ischemia or non-ischemia, values which may be varied according to the location of the $pCO_2$ measurement site.

The method of the invention will generally involve determination of $pCO_2$ in blood, on or in an organ, duct or tissue, or in the air flow from the lungs. In the latter case the $pCO_2$ sensor may be inserted into the body or may alternatively be in a hose one end of which is inserted into the body, i.e. within the airways.

The method of the invention may involve a single measurement of $pCO^2$ or, more preferably, may be used for continuous or repeated monitoring, especially of an at-risk patient, for example a patient in intensive care, undergoing or recovering from an organ or tissue transplant operation, assessed as having unstable angina, recovering from a coronary artery bypass operation, suffering trauma (e.g. of skeletal muscle), or suffering from hypovolemia (e.g. shock).

The comparison or threshold values for $pCO_2$ which may be used in the method of the invention may be values detected earlier in a continuous or repeated monitoring of a particular body site, using the sensor or they may be values detected for comparable body sites in the healthy, e.g. non-ischemic, body of a comparable subject (e.g. a subject of the same species and sex and similar age and weight).

The primary components of the sensor are an electrode chamber, a $CO_2$-permeable membrane forming at least part of the wall of the electrode chamber, first and second electrodes having surfaces within said. chamber (or providing internal surfaces to said chamber), and a liquid (generally substantially electrolyte-free water) in the electrode chamber in contact with the membrane and the first and second electrodes. The sensor includes or is connectable to an AC power supply, a conductance (or resistance) determining means, a signal generating means (which may be part of the determining means) and optionally a signal transmitting means. Moreover the sensor optionally includes surface attachment means by which it may be held in contact with a body surface (e.g. an organ, tissue or duct surface) or surface piercing means by the use of which it may be introduced through a body surface (e.g. an organ, tissue or duct surface).

In one embodiment of the sensor of the invention, a first of the two electrodes has a hollow cylindrical portion and the second is disposed within the hollow cylinder of the first, preferably at or near the axis thereof. The second electrode itself preferably has a solid cylindrical portion disposed within the hollow cylindrical portion of the first electrode. Where the first electrode has a hollow cylindrical portion, this can if desired form a wall of a closed electrode chamber containing liquid and the second electrode and having at least a wall portion provided by the $CO_2$-permeable membrane; however, it is preferred that the sensor has a closed electrode chamber having a further cylindrical wall surrounding, and preferably coaxial with, the two electrodes.

The cylindrical portions of the two electrodes preferably are axially coterminous at the end facing the membrane. They may contact the membrane if it is non-conductive but preferably are slightly displaced from it, e.g. by use of a spacer which may serve to limit or prevent deformation of the membrane.

The first electrode preferably has an outer diameter of the cylindrical portion of 0.8 to 2 mm, more preferably 1.2 to 1.6 mm. The second electrode preferably has an outer diameter of the cylindrical portion of 0.2 to 0.6 mm, more preferably 0.3 to 0.5 mm. The chamber preferably is hollow cylindrical with an internal length of 0.5 to 20 mm, more preferably 5 to 12 mm, and an internal diameter of 0.8 to 2.5 mm, more preferably 1.4 to 2.0 mm.

The membrane is preferably disposed substantially perpendicular to the electrode axis and spaced away from the cylindrical ends of the electrodes, for example by 0.05 to 0.5 mm, preferably by 0.1 to 0.2 mm.

The liquid film preferably covers the membrane to a depth of 0.0005 to 2 mm, more preferably 0.001 to 0.5 mm, when the membrane is horizontal.

Where the sensor is to be used in locations where it cannot be held with the membrane horizontal, the internal depth of the chamber is preferably kept small. In this way the liquid film will fill or almost entirely fill the chamber and so contact the membrane and both electrodes irrespective of the position in which the sensor is held.

The sensor of the invention will preferably include electrical leads from the two electrodes attachable directly or indirectly to a voltage or current applicator and measurement means. Moreover where the sensor is constructed without the liquid film, the chamber will be provided with means for insertion of the liquid, e.g. a sealable inlet port or a pierceable self-sealing substrate such as a rubber stopper. The sensor, with the exception of the membrane which must be exposed at least in part, may if desired be surrounded by a protective biotolerable material, e.g. a casing or a film coating, preferably of a non-conductive material. Likewise, where the sensor is intended for continuous monitoring of blood $pCO_2$, its surface may be coated with an anticoagulant, e.g. heparin. An anticoagulant coating may also be of advantage where the sensor is inserted into an organ and may induce clotting.

Where the sensor is constructed with the liquid film in place, the electrodes are preferably of an inert material such that the resistivity of the liquid will not change significantly with storage. Suitable materials include platinum (especially black platinum), stainless steel, silver, aluminium and carbon, particularly platinum and stainless steel (especially non-magnetic stainless steel where the sensor is to be used in imposed magnetic fields, for example within magnetic resonance imaging apparatus). In general inert electrodes which do not generate solvated ions are preferred. The thickness of the outer electrode and the diameter of the inner electrode will to a large degree depend on the strength of the electrode material used. Both electrodes are preferably of the same material to avoid a DC potential between the electrodes.

The liquid in the sensor may be any liquid capable of changing conductivity on reaction with (e.g. on dissolution therein of) carbon dioxide, e.g. a polar protic solvent capable of dissolving carbon dioxide and thereby producing ions. Water is preferred, however lower alkanols may be used. The liquid however is preferably as free as possible from dissolved ionic species and thus pure, e.g. double distilled, water is most preferred. As indicated above however, to such pure solvents it is desirable to add a small quantity of a strong acid, e.g. to maintain a pH of 6 or below. The quantity of liquid used should preferably be kept as small as possible as in this way the sensor is more rapidly responsive to external changes in $pCO_2$. However the quantity used should preferably be preselected, i.e. so that a group of similar sensors will each contain the same quantity of liquid. In the sensor as manufactured, any gas within the chamber should preferably be essentially $CO_2$ free, e.g. the liquid may have a nitrogen-filled head space. Before use, the sensor will preferably have been sterilised and packed in an airtight, e.g. foil, container to ensure that no accidental exposure to raised levels of $CO_2$ occurs. Also the atmosphere inside the container preferably should be saturated with water vapour to prevent evaporation.

The membrane may be any material which is permeable to $CO_2$, and essentially impermeable to the solvent of the liquid, any electrolyte and water. Teflon®, silicone rubber, polysiloxane, or other insulating polymer films may be used, e.g. at thicknesses of 0.5 to 250 um. The thicker the membrane, in general the slower the response time of the sensor will be. However the thinner the membrane the greater the risk of non-uniformities or of perforation or other damage. In general, membranes should be thinner for $pCO_2$ measurement in blood or in the airflow. The thicker membranes reduce capacitance effects from ions in organs. In any of the embodiments of the invention, a second (or further) $CO_2$ permeable membrane is preferably mounted adjacent the membrane which contacts the liquid in the sensor. Between the two membranes there may be an air (or other gas) gap (optionally including a gas-permeable spacer) or more preferably a gel especially one containing a sequestering agent (e.g. a chelating agent) that serves to bind anions or cations entering the gap through the external membrane or through holes or defects therein. (In this way drift in long term measurements on organs or tissues may be reduced or avoided). Such a double membrane construction also avoids the capacitance effects of ions in organs and reduces risk of accidental inner membrane perforation and as a result the thinner membranes may be used for $pCO_2$ measurement in organs. Conveniently however the membrane will be about 0.5 to 10 um, preferably about 1 um for blood or airflow $pCO_2$ measurement and 1 to 50 um, preferably 2 to 40 um for organ $pCO_2$ measurements. It will be appreciated that for detecting ischemia, a response time as long as 10 minutes may be acceptable.

The walls of the chamber of the sensor of the invention may be of any suitable material, e.g. plastics. preferably the material should be capable of withstanding conditions normally used in sterilisation, e.g. radiation sterilization (for example using γ-radiation) or thermal sterilization (for example using temperatures of about 121° C. as used in autoclave sterilisation). In the case of thermal sterilization, the liquid will generally be sterile filled into the sensor after sterilization. The walls of the chamber and the membrane may be of the same material, e.g. Teflon® machined to have self-supporting walls and a thinner gas-permeable end membrane.

In a further, preferred, embodiment the sensor of the invention comprises a $CO_2$ permeable membrane which provides one face of a liquid containing chamber in which the liquid containing volume is defined by the membrane, a first electrode, a second electrode and insulating wall means, the wall means, electrodes and membrane defining (i) a small cross-sectional area of the liquid (across the direction of current flow) at a membrane contacting portion of the liquid, (ii) a large surface area membrane-contacting portion of the liquid and (iii) relatively large electrode:liquid contact portions. This may be achieved by placing the electrodes in wells in an insulator (which may or may not be provided with channels between the wells) with a central insulator portion which is more closely adjacent the membrane such that liquid resistance is higher in a membrane-adjacent portion of the electrical flow path than in the electrode adjacent portions. For this purpose, the electrodes may conveniently be formed as layers within a sandwich electrode:insulator construction or as wires or deposits placed in grooves or indentations in an insulator substrate.

The sensor device of the invention can thus be made small enough for insertion into a respiratory hose, into the vasculature or into or onto the surface of an organ, tissue or duct; it is cheap and simple and may have single-use application (i.e. it can be disposable) or alternatively it may be sterilised and reused. The response time to $pCO_2$ changes is rapid (e.g. 10 minutes, preferably 5 minutes, or more preferably 30 seconds, or less) and problems of drift encountered with conventional blood gas electrodes are avoided. The device is thus well-suited for the clinical environment.

Where the sensor is to be reused, the membrane and electrodes are preferably separable to permit replacement of the liquid. Thus for example the membrane may be replaceable, e.g. taking the form of a disc disposed between the body and a sealingly engageable and removable end cap of the chamber. In this embodiment, between uses, the end cap and membrane will be removed, the solvent replaced, and the end cap and membrane disc (either as two components or an integral unit) replaced. During or after this procedure, the sensor will be sterilized. More preferably however the sensor will be a single-use, disposable device.

For in vivo measurement of $pCO_2$ (except for in vivo blood gas measurements) no widely commercially available technique has yet been developed. Several techniques have been tried in animal experiments (ISFET electrodes, infrared absorption and others), but all of them have shortcomings. (ISFET electrodes have been used in humans but without satisfactory results). Among weaknesses are size, drifting and high cost of manufacturing. In contrast the sensors of the invention are inexpensive to produce, will have minimal drifting and with proper quality of de-ionized water, calibration may not be necessary. Using a small volume of water and preferably carbonic anhydrase, they will be fast enough for measuring end-expiratory $pCO_2$. The sensors can be small and can be disposed in the main stream in a respirator hose. consequently, there will be no need to suction out gas from the ventilator hoses as is now done with most techniques. This is a definite advantage, particularly in the monitoring of children whose respiratory volumes are small. Thus the sensors of the invention have the potential of being applicable for in vitro, in vivo and end-expiratory measurements of $pCO_2$. They can both be used for ventilatory monitoring, intravascular $pCO_2$ measurement and for detection of ischemia at the organ level.

Besides in vivo and ex vivo uses, the sensors of the invention may be used in other situations where $pCO_2$ measurement is desired, in particular uses not associated with animate test subjects, e.g. in vitro measurements of pCO2 in gases or liquids, for example drinks or effluent gases. In further aspects the invention provides a method of determining $pCO_2$ or pressure in such in vitro uses using sensors according to the invention.

It is especially preferred that the sensors of the invention be applied to the surface of a tissue, duct or organ of interest to determine $pCO^2$ for that tissue, duct or organ. This is feasible since $CO_2$ diffuses out of tissues, ducts and organs such as the heart, liver, kidney, brain, gut and muscle. For these purposes it is desirable that the sensor include surface attachment means (e.g. a flexible or perforated flange which may be sutured to the organ, tissue or duct surface; a flexible tissue-adhesive carrying flange; an adjustable clip; a flexible barb etc). In this embodiment, the electrode chamber is preferably disc-shaped with the $CO_2$ permeable membrane on one of the faces of the disc. Such $pCO_2$ sensors are in themselves novel and form a further aspect of the invention. Viewed from this aspect the invention provides a $pCO_2$ sensor having a disc-shaped electrode chamber one face of which is provided at least in part by a $CO_2$ permeable membrane, said sensor further comprising surface attachment means.

Where alternatively the sensor is to be inserted through a body surface (e.g. an organ, tissue or duct surface) it will conveniently be provided with surface piercing means, for example having the electrode chamber in the shaft of an elongate sharp-ended sensor. Such sensors are also novel and form a further aspect of the invention. Viewed from this aspect the invention provides a $pCO_2$ sensor having an elongate body portion with sharp body surface piercing means at a first end thereof and containing spaced away from said first end an electrode chamber at least a portion of an exposed wall whereof is provided by a $CO_2$ permeable membrane.

The sensors of the invention are relatively inexpensive and so, unlike prior art sensors, may be single-use devices. Moreover the electrode chamber can be made extremely small without difficulty (unlike the prior art glass electrode containing sensors for which miniaturization poses insuperable impedance problems).

The mechanism by which $pCO_2$ is determined using the sensor device of the invention is straightforward. In a pure protic solvent, e.g. water, the electrical resistance is high because of the paucity of ionic species. Addition of $CO_2$ results in formation (with water) of $H^+$ and $HCO^-_3$ ions and thus a reduction in the electrical resistance. Since the only factor responsible for reduction in resistance in the sensor is $CO_2$ passing through the membrane, the change in resistance enables $pCO_2$ to be measured. (In the pressure sensor of the invention on the other hand the change in resistance arises from the change in cross sectional area of the electrical path through the liquid due to pressure induced deformation of the membrane).

From the equilibrium constant for the $H_2O+CO_2$ to $H^++HCO_3^-$ equilibrium, $CO_2$ concentration is equal to $\alpha pCO_2$ (where $\alpha$ at 25° C. is 0.310). The electrical conductivity for protons is $G_{H+}$=349.8 S·cm²/mol, that for hydroxyls is $G_{OH-}$=198.3 S·cm²/mol and that for bicarbonate is $G_{HCO3-}$=44.5 S·cm²/mol. The concentrations of $H^+$ and $OH^-$ vary inversely, and the concentrations of $H^+$ and $HCO_3^-$ are directly proportional to $pCO_2$. The total conductance of the solution is thus effectively proportional to $pCO_2$ since the contribution of OH⁻ is minimal. The conductivity of the solution $G_{solution}$ is thus given by $$G_{solution}=\theta_{H+}[H^+]G_{H+}+\theta_{OH-}[OH^-]G_{OH-}+\theta_{HCO-3}[HCO_3^-]G_{HCO3-}$$

where $\theta_{H-}$, $\theta_{OH-}$, and $\theta_{HCO-3}$ are the activity coefficients for the three ionic species.

Table 1 below shows, by way of example, measured $pCO_2$ and pH values and corresponding calculated values for $H^+$, $OH^-$, and $HCO_3^-$ concentrations showing the increase of $H^+$ and $HCO_3^-$ with increasing $pCO_2$.

| Sample number | $pCO_2$ (kPa) | pH | [H⁺] (mmol/l) | [OH] (mmol/l) | $HCO_3^-$ (mmol/l) |
|---|---|---|---|---|---|
| 1 | 6.38 | 5.141 | 7.23E−06 | 1.38E−09 | 7.23E−06 |
| 2 | 9.64 | 5.060 | 8.71E−06 | 1.15E−09 | 8.71E−06 |
| 3 | 15.37 | 4.891 | 1.29E−05 | 7.78E−10 | 1.29E−05 |
| 4 | 25.88 | 4.760 | 1.74E−05 | 5.75E−10 | 1.74E−05 |
| 5 | 31.48 | 4.664 | 2.17E−05 | 4.61E−10 | 2.17E−05 |

($pCO_2$ and pH measured with a standard blood gas analyser, ABL ® System 625 at 37° C.)

The electrical conductivity is measured in the solvent film in the sensor of the invention. This can be done by applying a constant voltage (or current) to the electrodes and measuring the current (or voltage) changes which correspond to changes in conductivity as $CO_2$ enters the solvent through the membrane. Preferably however an alternating sine wave function voltage with a constant peak value is applied and the voltage drop over the two electrodes is measured. The solution conductivity is then equal to the current passed through the electrode divided by the voltage drop over the two electrodes.

BRIEF DESCRIPTION OF THE DRAWINGS

An embodiment of the invention will now be described further with reference to the accompanying drawings, in which:

FIGS. 14A and 14B are a sectional view and a perspective view of a sixth $pCO_2$ sensor according to the invention.

DETAILED DESCRIPTION OF INVENTION

Figure 1:
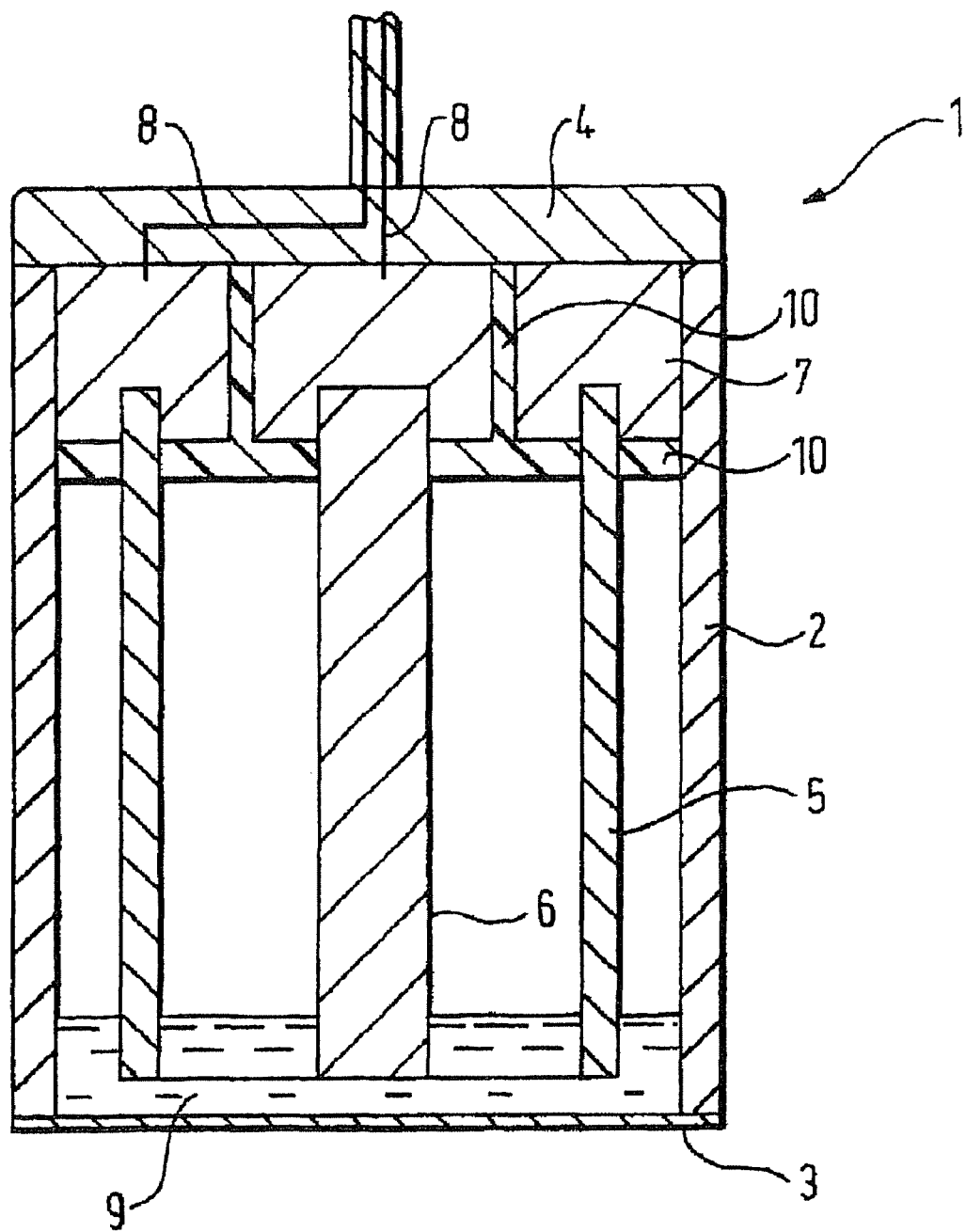
FIG. 1 is a schematic cross-sectional view of a sensor according to the invention.

Referring to FIG. 1 there is shown a sensor 1 comprising a cylindrical casing 2 of stainless steel having an external diameter of 2.0 mm and an internal diameter of 1 mm and a length of 3 mm. Casing 2 is sealed at the lower end by Teflon® membrane 3 and at the upper end by cap 4. Within casing 2 are disposed two electrodes 5 and 6 (e.g. carbon electrodes) and an insulated electrode holder 7. Inner electrode 6 has an external diameter of 0.4 mm while outer hollow cylindrical electrode 5 has a wall thickness of 0.01 mm and an external diameter of 1.4 mm. Electrode holder 7 has sections, mutually insulated by insulator 10, holding the two electrodes and is connected to leads 8 which pass through cap 4 to a current/voltage applicator and measurement device (not shown).

Covering membrane 3 there is a thin film 9 of doubly distilled water, 0.001 mm deep. This may be achieved by disposing a 1 um porous spacer of cuprophane (a dialysis membrane) (or more preferably a plastics net) to the interior side of the covering membrane.

Figure 2:
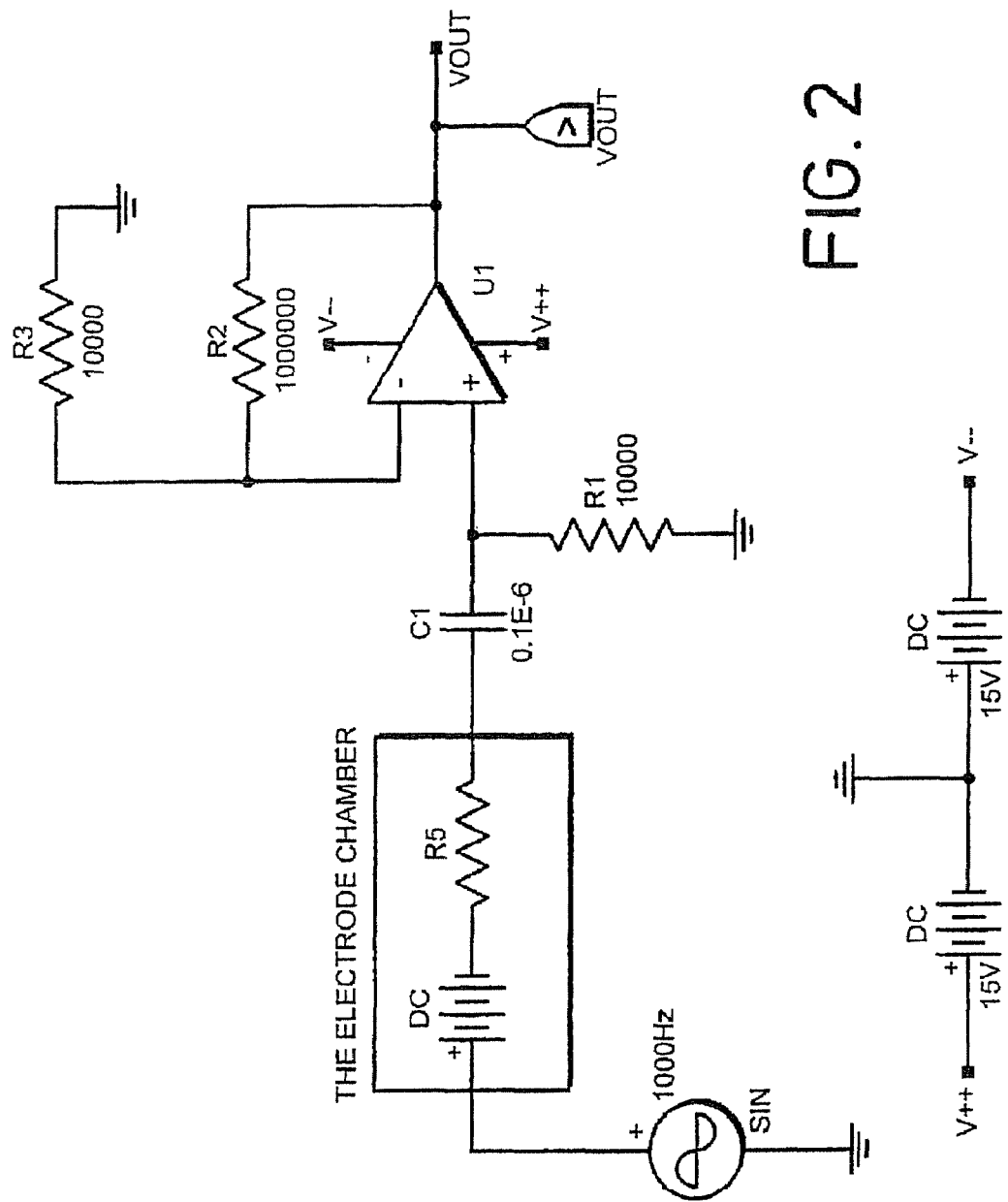
FIG. 2 is a circuit diagram for the measurement circuit for the sensor of FIG. 1.

Referring to FIG. 2 there is shown a pCo2 measurement circuit for use with the sensor of FIG. 1. An AC current of frequency 1 kHz is applied to electrodes 5 and 6 when sensor 1 is dipped into the test substance. (Use of an AC current avoids electrolysis).

The sensor of FIG. 1 was tested out in vitro using water with different $pCO_2$ values (as determined with an ABL System 625 blood gas machine) produced by bubbling 100% $CO_2$ gas through doubly distilled water for different times until the desired $pCO_2$ values were attained.

Measurements were carried out using a lock-in amplifier (SR 850) combined with the circuit of FIG. 2. The first stage of this circuit contains a high pass filter (150 Hz) to remove DC signals. The second stage is an AC-amplification to increase the resolution of the measurements according to the formula:

$$\text{amplification}=R_2/R_3+1.$$

The input voltage from the signal generator was 6 mV and the values of resistors $R_1$, $R_2$ and $R_3$ were respectively 1 MΩ, 50 kΩ and 10 kΩ.

Figure 3:
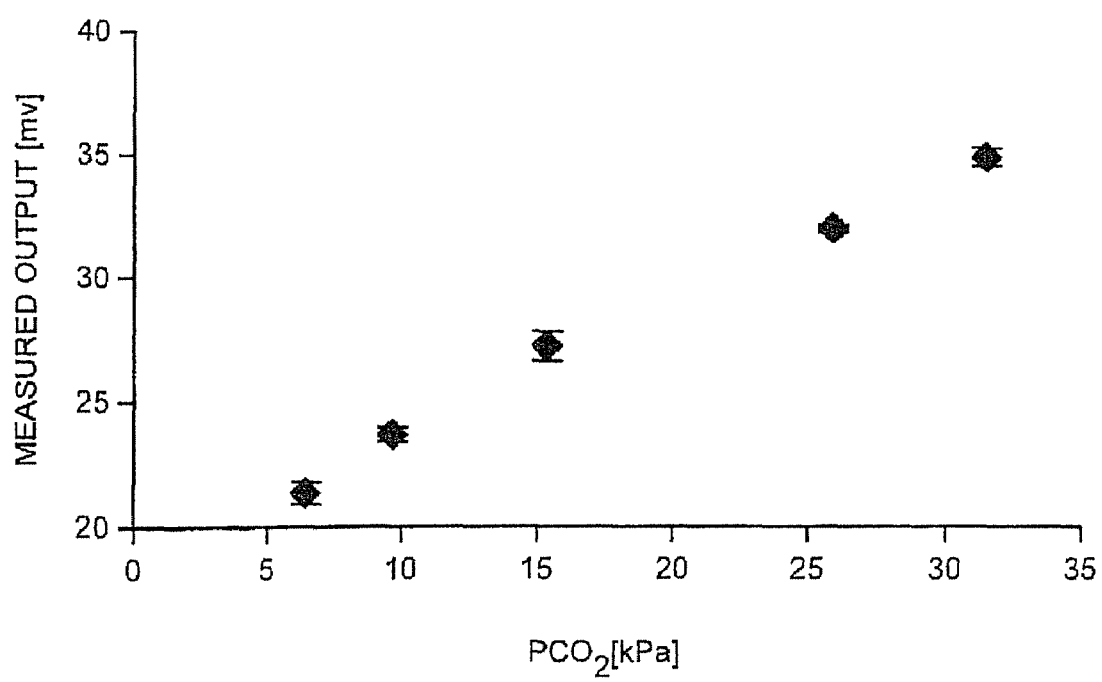
FIG. 3 is a plot of measured output voltage for the sensor of FIG. 1 against $pCO_2$.

The output voltage was measured at different $pCO_2$ values in the range 6 to 31.5 kPa (see Table 1 above). Measurement was repeated six times at each value to ensure reproducibility. During measurement, the current density varied from 1 to 17 uA/cm² which is within the limits of electrode linearity. The measured output voltages plotted against $pCO_2$ are shown in FIG. 3.

Figure 4:
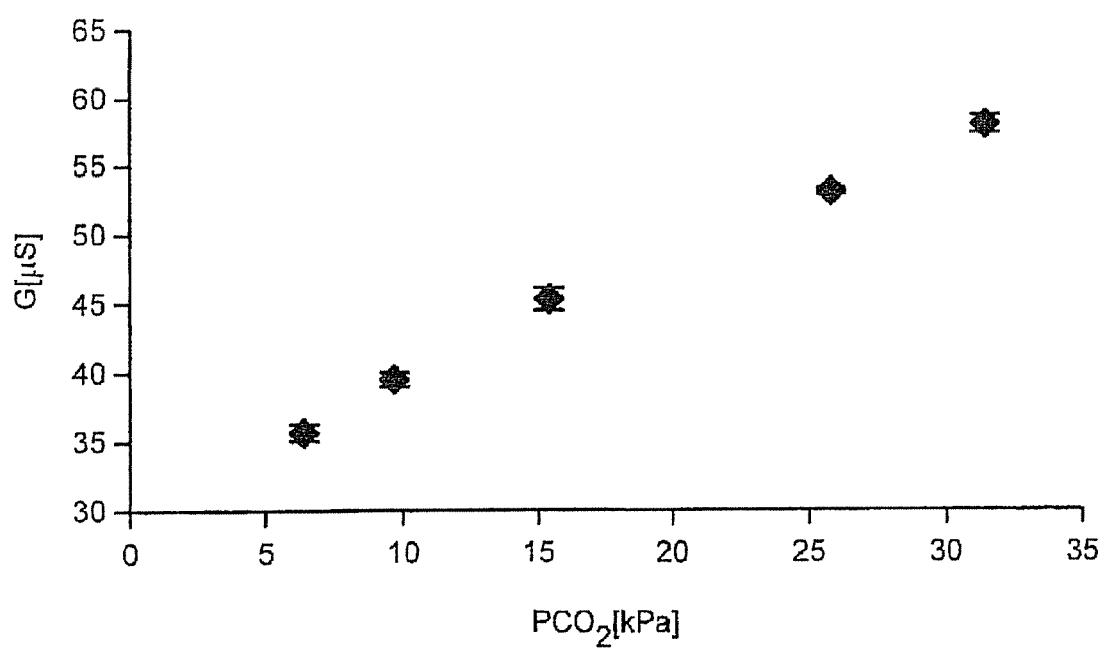
FIG. 4 is a plot of measured conductance for the sensor of FIG. 1 against pCO2.
Figure 5:
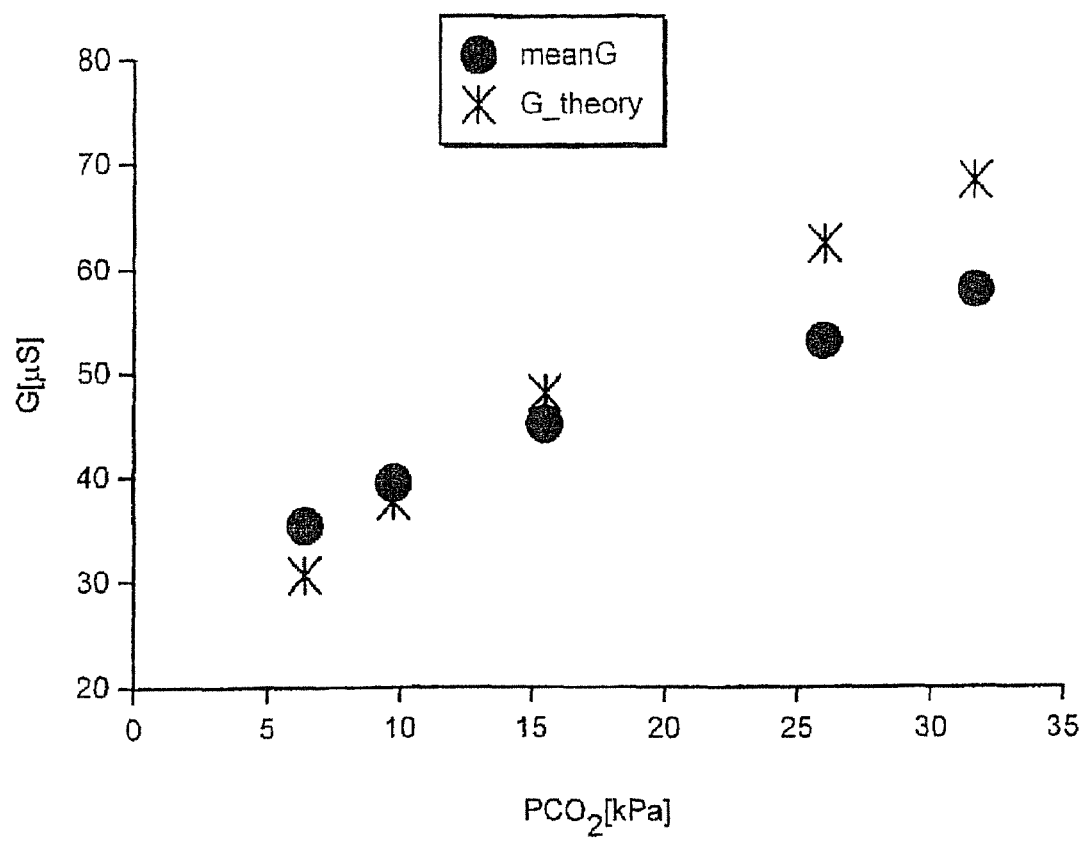
FIG. 5 is a plot of the measured and theoretical values for conductance against pCO2.

The conductance as a function of $pCO_2$ was calculated by dividing the current through the electrode by the voltage drop over the electrodes and is shown in FIG. 4. Applying the equation for the value of $G_{solution}$ solution given above, theoretical (*) and mean measured (●) values of conductance where compared (see FIG. 5). As can be seen, the correlation was good.

Figure 6A:
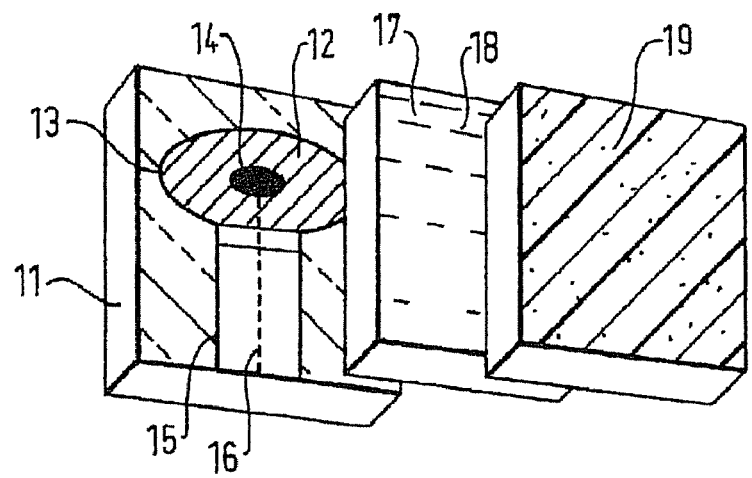
FIGS. 6A and 6B are schematic exploded and cross-sectional side views of a second $pCO_2$ sensor according to the invention.
Figure 6B:
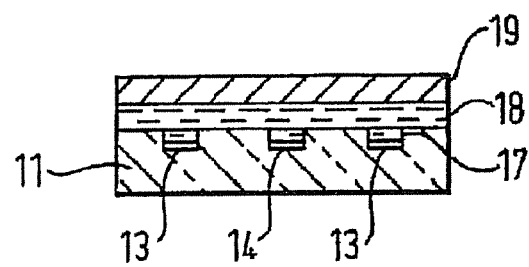

A further embodiment of the sensor of the invention is shown in FIGS. 6A and 6B of the accompanying drawings. In this embodiment, a substrate 11 of a non-conductive material (e.g. silicon or more preferably glass) is formed (e.g. machined or etched) to provide a surface of a liquid enclosing zone 12 on or about which first and second electrodes 13 and 14 are laid or deposited, e.g. as wires or printed or vapor deposited conductors. Desirably the liquid enclosing zone has recesses into which the electrodes are placed so as to ensure that the liquid depth is greater at those locations than in the intervening area. The electrodes are electrically connected to a power source (not shown) by leads 15 and 16 which may be covered by an insulator (not shown) to ensure that current flow in the liquid enclosing zone is between the electrodes and through the liquid 17 rather than between the leads to the electrodes. The electrodes are desirably 1 to 3 mm in width parallel to the surface of substrate 11 and may for example be formed from platinum, e.g. black platinum, or silver or aluminium. The substrate may be of any appropriate depth, e.g. 3 to 50 mm. The gap between the electrodes, which as shown are concentric, is preferably at least 0.5 mm, e.g. 0.5 to 3 mm. Over the substrate surface is placed a porous spacer layer 18, e.g. a cuprophane membrane (or more preferably a plastics net) which may have a dimension in the micron range, e.g. a thickness of 1 um. This preferably abuts the surface of the substrate between the electrodes and optionally the substrate surface outside the outer electrode 13. This spacer serves both to contain the liquid 17 and to maintain a fixed depth of liquid between the substrate surface and a $CO_2$ permeable membrane 19 which is disposed over the spacer. About its periphery, membrane 19 is sealed (not shown) directly or indirectly to substrate 11 to define a liquid enclosing chamber. Membrane 19 is conveniently of Teflon or polysiloxane and suitably is 0.5 to 250 um thick, preferably 1 to 50 um thick.

Figure 7A:
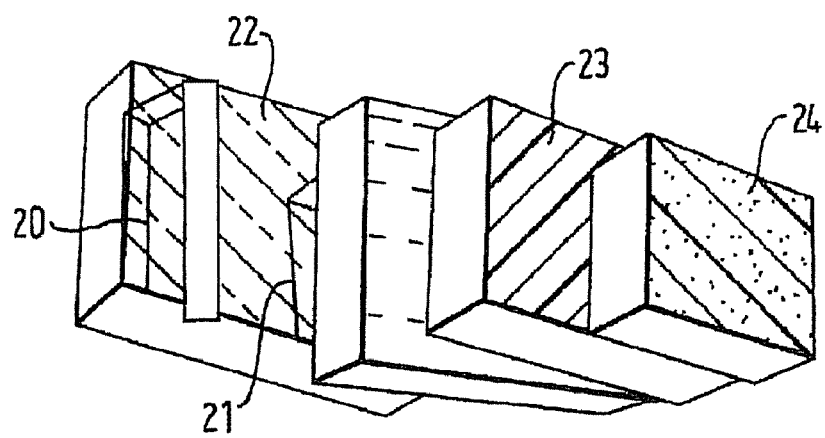
FIGS. 7A and 7B are schematic exploded and cross-sectional side views of a third $pCO_2$ sensor according to the invention.
Figure 7B:
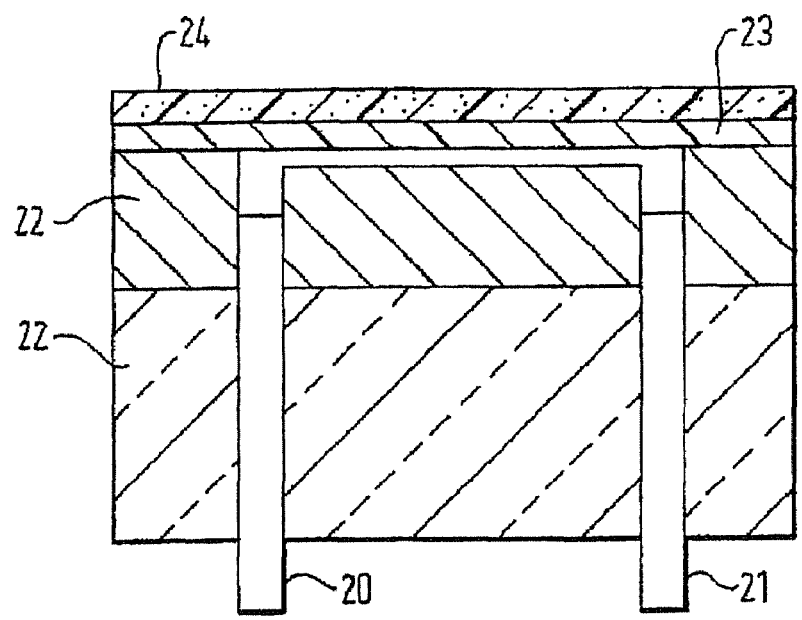

A still further embodiment of the sensor of the invention is shown in FIGS. 7A and 7B where first and second electrodes 20 and 21 are placed in a substrate (e.g. of glass, silicon or Teflon) 22, e.g. in channels etched or machined therein or in a sandwich like structure. The electrodes are parallel, preferably about 1 mm in length, and preferably spaced apart by at least 1 mm, e.g. 1 to 3 mm. The substrate between the electrodes is preferably raised relative to the electrodes and conveniently is either flush with or slightly lower than the surface of the substrate beyond the electrodes. Over the substrate and electrodes is disposed a porous spacer 23, e.g. a 1 um thick cuprophane membrane (or more preferably a plastics net) and over the spacer is sealingly disposed a $CO_2$ permeable membrane 24, e.g. a 1 um thick Teflon membrane. The chamber defined by the $CO_2$ permeable membrane, the substrate and the electrodes is filled with substantially electrolyte free water adjusted to a pH slightly below 7 by addition of HCl.

To produce a pressure sensor according to the invention spacer 23 may be omitted or may be provided with an aperture over the portion of the substrate between the electrodes and gas permeable membrane 24 replaced by a gas impermeable membrane. In this embodiment, the surface of the substrate between the electrodes is preferably 0.5 to 2 um away from the inner surface of the gas impermeable membrane.

Figure 8:
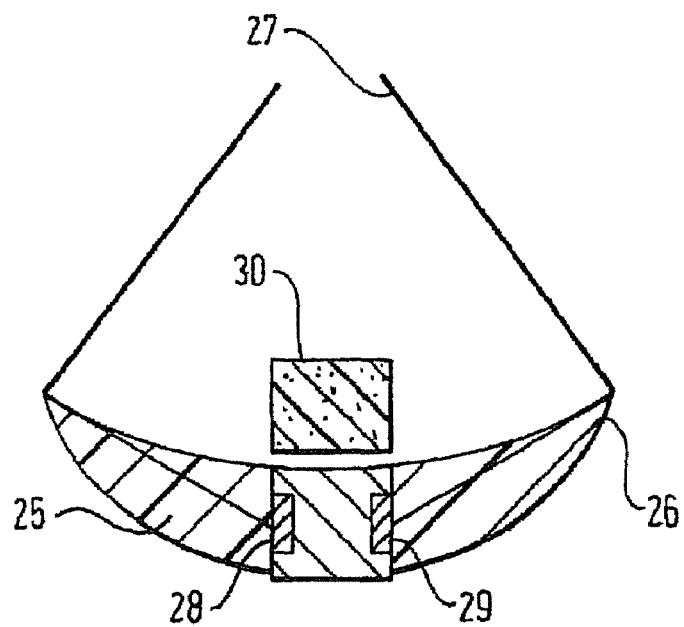
FIG. 8 is a schematic view of a pCO2 sensor according to the invention in a form suitable for insertion through an organ surface.

In FIG. 8, there is shown a body surface (e.g. organ surface) piercing sensor according to the invention. The sensor comprises a curved elongate body member 25 of a plastics material having at one end a sharp, piercing portion 26 and having connected at the other end wires (leads) 27 leading to a power source (not shown). In a central portion of the body member two electrodes 28,29 are disposed which are electrically connected to wires 27 and covered by a spacer (not shown) and by a $CO_2$ permeable membrane 30 (shown removed). The electrode/spacer/membrane assembly may typically be constructed as described above in relation to FIG. 7.

The body member is typically about 2 to 6 mm in length and one, or more usually an array, of such sensors may be placed into the surface of an organ during surgery with the leads emerging together through a surgical incision in the skin, generally within or adjacent the post-operative drainage duct. When monitoring of the patient is to cease, the sensors may simply be withdrawn by gentle pulling of the wires 27 outside the body.

Figure 9:
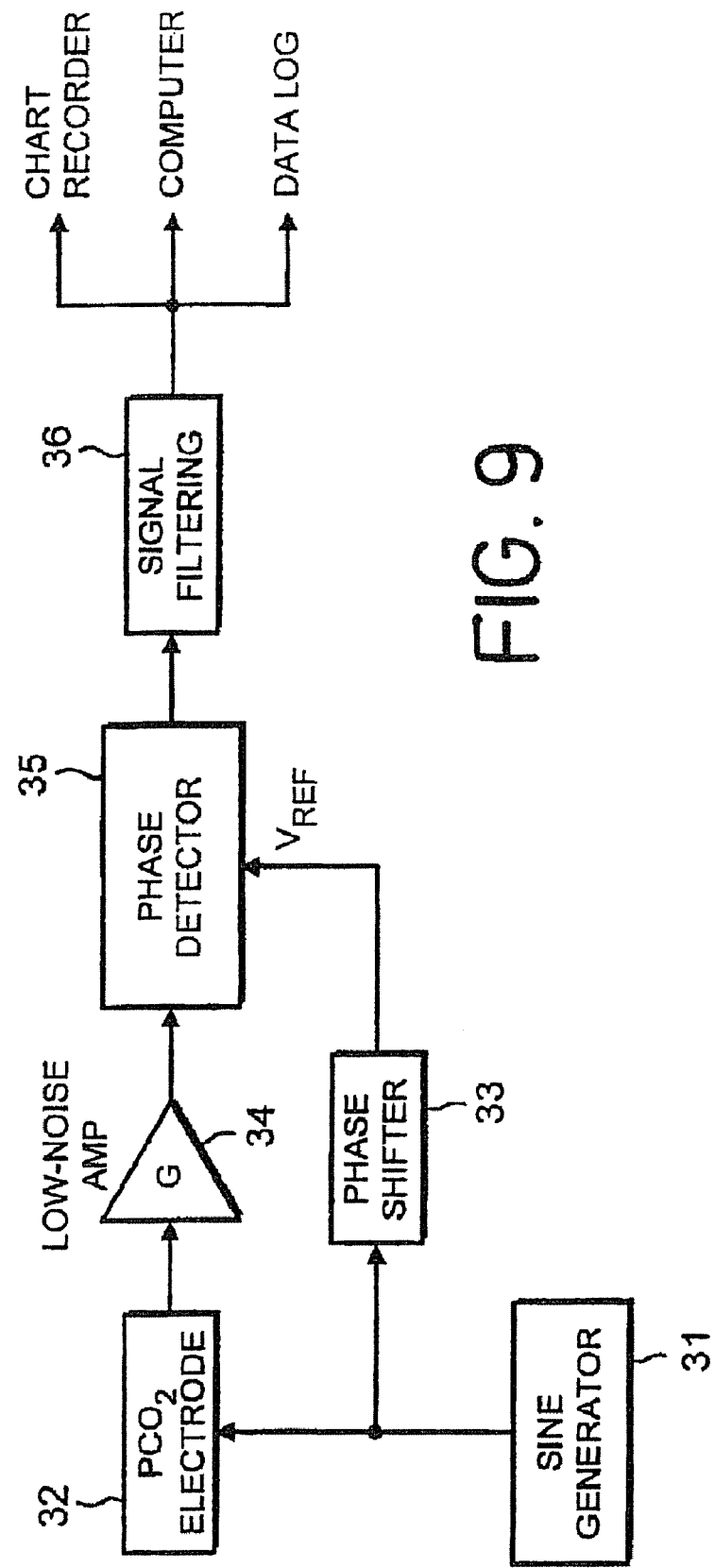
FIG. 9 is a schematic plan of the electronics for operating a pCO2 sensor according to the invention.

FIG. 9 is a schematic representation of electronics suitable for operating the sensors of the invention. An AC current is generated by sine generator 31 and fed to one of the $pCO_2$ sensor electrodes 32 and to a phase shifter 33. The signal from the other $PCO_2$ electrode 32 is passed to a low noise amplifier 34 and from there to a phase detector 35 where its phase is compared with that of a reference signal generated by phase shifter 33. Out of phase components, i.e. undesired components, of the amplified signal are rejected and the remaining portion of the amplified signal is fed to signal filter 36 to remove low frequency components. The filtered signal is proportional to $pCO_2$ (or conductance) and is passed on for recordal or further manipulation, e.g. by a chart recorder, a computer or a data logger.

Figure 10A:
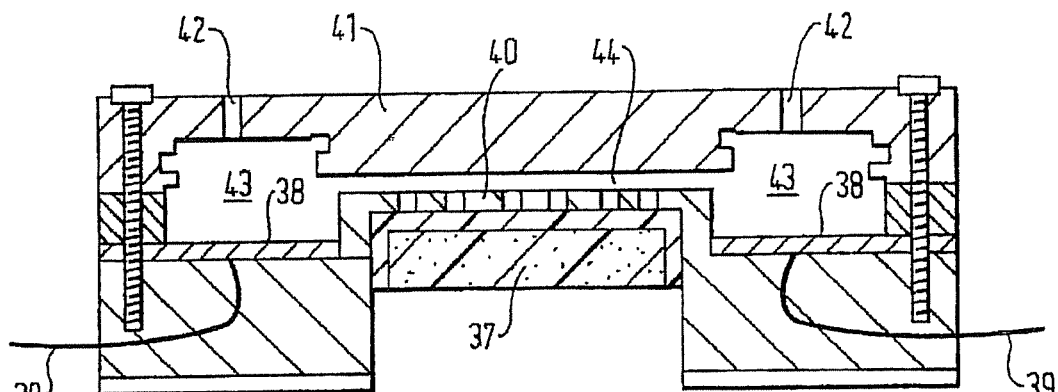
FIGS. 10A to 10C show a fourth $pCO_2$ sensor according to the invention in side sectional view (FIG. 10A), plan sectional view from above (FIG. 10B) and plan sectional view from below (FIG. 10C)
Figure 10B:
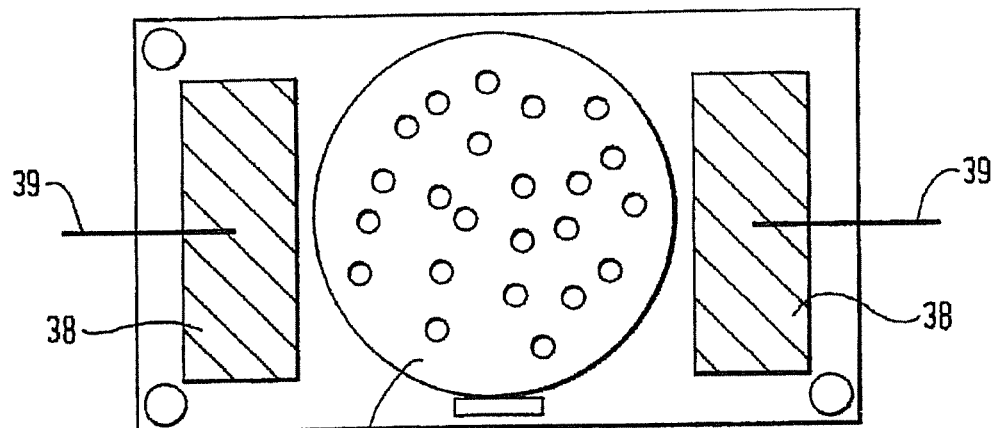
Figure 10C:
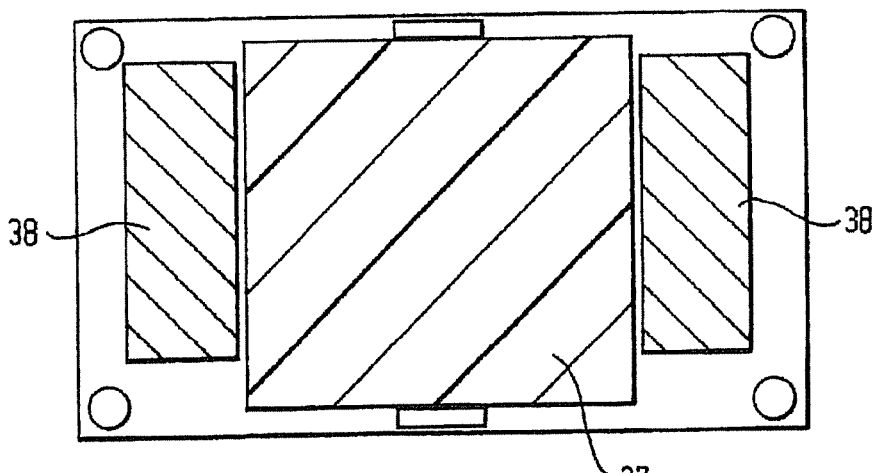

The $pCO_2$ sensor shown in FIGS. 10A-10C comprises a tightly-stretched $CO_2$ permeable membrane 37 and two electrodes 38 which are connected to the external sensing electronics (not shown) by wires 39. The membrane 37 is mounted against a grid 40 in which are defined a plurality of holes through which $CO_2$ passing the membrane 37 can travel. The water in the holes in the grid 40 does not affect the conductivity measurements. The grid 40 provides mechanical support for the membrane 37 to prevent pressure changes in the water in the sensor while allowing the passage of $CO_2$ therethrough.

The sensor is provided with a cover portion 41 which has defined therein two filler holes 42 through which double distilled water can be passed to fill the water chambers 43 above each electrode 38. Between the water chambers 43 and defined between the cover portion 41 and the grid 40 is a bridge chamber 44 which fills with water when the water chambers are filled and provides a relatively low volume/high surface area region for absorption of $CO_2$ passing through the membrane 37. The provision of the bridge chamber 44 permits a the sensitive sensor because the water in the bridge chamber 44 forms the conductive path between the electrodes 38 in use of the sensor, and the relatively low volume and high surface area of this region ensures a relatively large increase in conductivity with $CO_2$ passing through the membrane 37.

However, the major advantage of the arrangement shown in FIGS. 10A-10C is that the surface area of the water in contact with the electrodes is relatively high to reduce electropolarisation effects.

It is to be noted that the water chambers 43 extend above the horizontal level of the bridge chamber 44. This ensures that any air bubbles in the water are retained in the water chambers 43 and do not affect the conductivity of the water in the bridge chamber 44.

Figure 11:
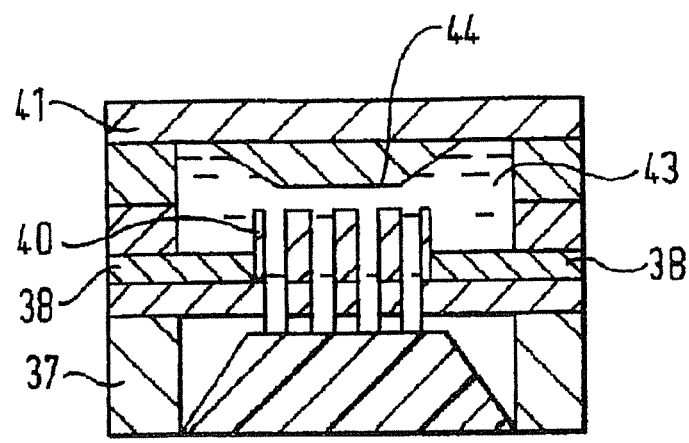
FIG. 11 shows a fifth pCO2 sensor according to the invention in side sectional view.

The $pCO_2$ sensor shown in FIG. 11 is composed of silicon layers bonded together with silicon dioxide and has silver/aluminium electrodes 38. The structure of this sensor is similar to that of the sensor of FIGS. 10A to 10C and like reference numerals have been used for corresponding parts.

Figure 12:
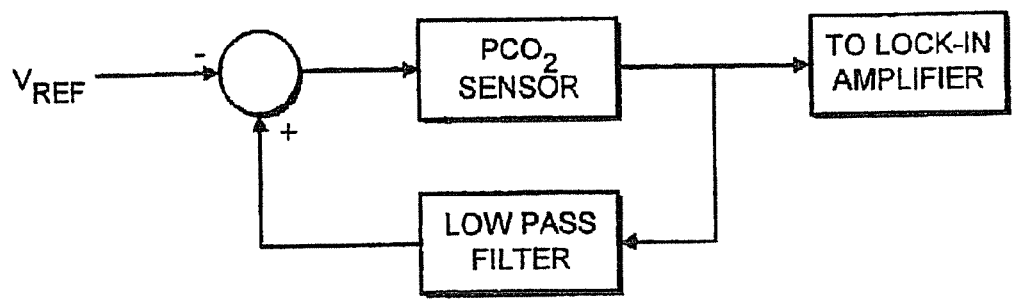
FIG. 12 shows schematically an arrangement of the sensing electronics for a sensor according to the invention.

FIG. 12 shows a schematic diagram of an improvement to the sensor electronics for the $pCO_2$ sensor according to the invention. It has been noted that the $pCO_2$ sensor generates a small DC voltage due to electrolytic effects between the electrodes and the ions in the water. However, pre-amplification of the signal through the $pCO_2$ sensor can increase the DC current through the sensor to such an extent that the electrodes can degrade resulting in drift of the sensor.

In the basic arrangement shown in FIG. 2, the capacitor C1 acts to block DC current passing through the sensor and the pre-amplification stage, to prevent drifting problems arising. However, the capacitor results in an extra phase addition to the AC signal which can cause errors in the detection signal measured by the lock-in amplifier. Furthermore, a large capacitor is difficult to incorporate into an application specific integrated circuit (ASIC).

FIG. 12 schematically shows an alternative to the capacitor arrangement of FIG. 2 in the form of a servo mechanism. According to this arrangement, the output of the pre-amplifier is fed back to its input via a low pass filter. Thus, only DC components of the output are fed back and cancel any DC current drawn through the $pCO_2$ sensor. In this way, it is ensured that there is no DC current through the $pCO_2$ sensor which would degrade the electrodes.

Figure 13:
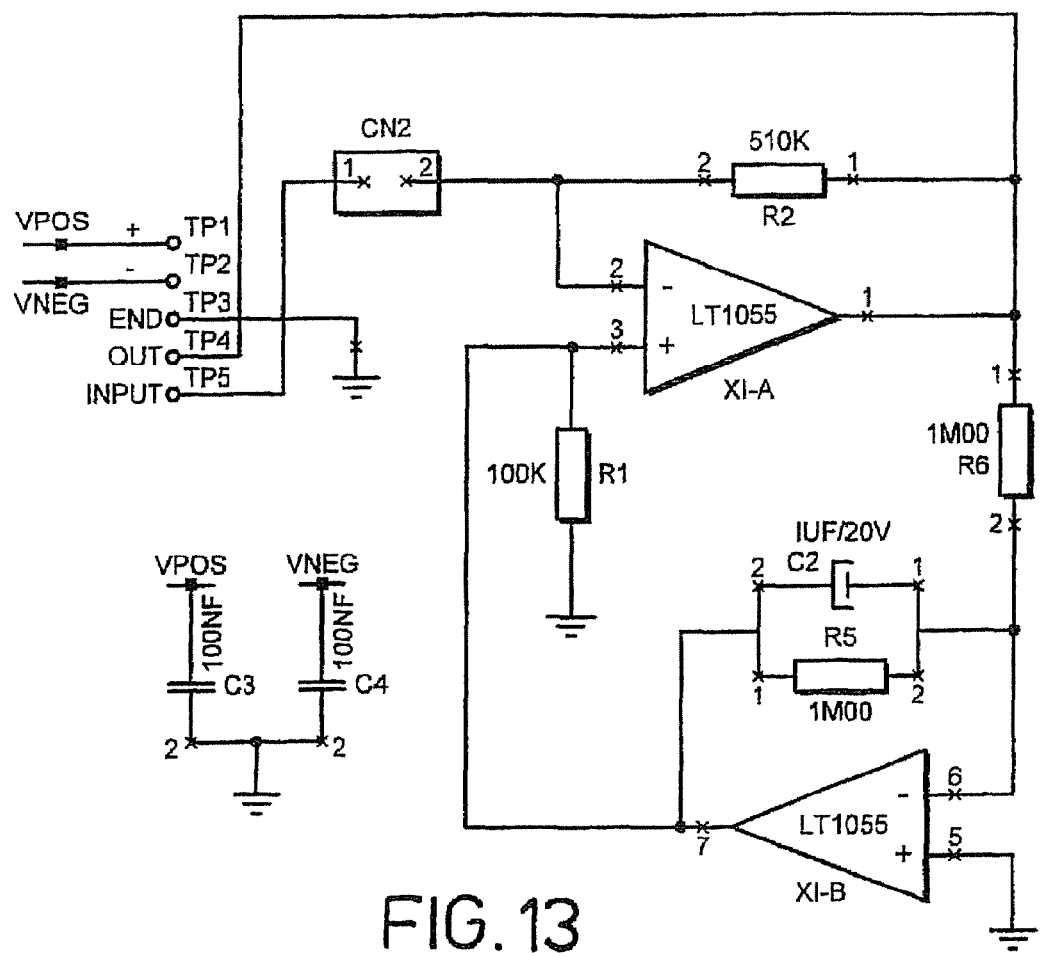
FIG. 13 is a circuit diagram showing an embodiment of the sensing electronics of FIG. 12.

FIG. 13 shows a circuit diagram of an arrangement to implement the low pass filter feedback described above. The alternating reference voltage is input at connector TP5 and the output voltage to the lock-in amplifier is output at connector TP4. The $pCO_2$ sensor is represented as component CN2 and is in series between the input and output of the circuit with a load resistor R2. An op-amp X1-A is connected with its inverting input and output in parallel across the load resistor R2.

The DC component of the op-amp output voltage $V_{OUT}$ is passed by means of a low pass filter arrangement (R6, X1-B, C2, R5) with a cut-off frequency of 1 Hz to the non-inverting input of the op-amp X1-A. Thus, when the output voltage $V_{OUT}$ includes a DC component positive feedback via the low pass filter causes the output voltage $V_{OUT}$ to rise. This increases the voltage across the load resistor R2 which causes the voltage at the inverting input of the op-amp X1-A to rise to compensate for the increased output voltage. It will be seen therefore that this arrangement always causes the voltages at the inputs of the op-amp X1-A to tend to be equal and for frequencies under 1 Hz the output voltage $V_{OUT}$ from the op-amp X1-A equals the voltage at the inverting input of the op-amp. The voltage across the feedback resistor R2 is therefore zero, for frequencies under 1 Hz and no DC current is drawn from the input. Consequently, all AC currents will pass without any phase shift, while frequencies under 1 Hz will be attenuated to virtually zero level.

The arrangement shown in FIG. 13 has the advantage that it does not require a large capacitor and can therefore be formed easily as part of an ASIC. In preferred embodiments, therefore, the sensor comprises a feedback arrangement for feeding back low frequency, for example DC, components of the output voltage from the sensor in order substantially to cancel low frequency, for example DC, current through the sensor.

The sensor shown in FIGS. 14A and 14B is of a cylindrical configuration but operates on the same principles described in relation to the other embodiments of the $pCO_2$ sensor. The sensor has a plastic core 45 which mounts two ring electrodes 46 which are connected to the external sensing circuitry (not shown) via wires 47. The wires 47 are shielded to prevent cross-talk.

An outer cylinder 48 has defined therein a plurality of holes and acts in the same way as the grid 40 shown in FIGS. 10A-10C to support the gas permeable membrane 49. Rings 50 hold the membrane 49, cylinder 48 and plastics core 45 in position in the sensor. As shown in FIG. 14B the sensor is intended to be received in a catheter so that it can be inserted superficially in an organ of interest. In order to make the catheter biocompatible it may be coated with polyethylene.

The measuring film of deionised water is located between the plastics core 45 and the membrane 49.

What is claimed is:

1. A carbon dioxide sensor, comprising:
   a closed chamber including as a wall portion thereof a substantially water-tight, carbon dioxide-permeable membrane;
   two electrodes disposed in said chamber; and
   a film of substantially electrolyte-free liquid disposed in said chamber capable of simultaneously contacting said membrane and both of said electrodes;
   wherein said electrodes are configured to receive an alternating electrical potential from a supply source other than said electrolyte-free liquid.

2. The sensor as claimed in claim 1 further comprising means for applying an alternating electrical potential to said electrodes whereby to cause an alternating current in said liquid, and means for generating a signal indicative of the conductance of said liquid, wherein said liquid is reactive with carbon dioxide to alter its conductance.

3. The sensor as claimed in claim 1, wherein said chamber is arranged such that in the electrical path between said electrodes through said liquid the electrical resistance of said liquid at each of said electrodes is less than in a portion of said liquid in contact with said membrane.

4. The sensor as claimed in claim 1, wherein said chamber is disc-shaped with one face provided at least in part by said membrane, said sensor further comprising surface attachment means.

5. The sensor as claimed in claim 1, wherein having an elongate body portion with sharp body surface piercing means at a first end thereof and containing spaced away from said first end said chamber at least a portion of an exposed wall that is provided by said membrane.

6. The sensor as claimed in claim 1, wherein said chamber is cylindrical with an outer wall provided at least in part by said membrane, said sensor preferably being provided with a catheter for attachment to an organ.

* * * * *